United States Patent
Nilsson (10) Patent No.: US 9,402,810 B2
(45) Date of Patent: *Aug. 2, 2016

(54) POUCH CONTAINING NICOTINE IN FREE SALT FORM

(71) Applicants: TILLCE AB, Strandbaden (SE); WM17 HOLDING AG, Baar (CH)

(72) Inventor: Per-Gunnar Nilsson, Malmo (SE)

(73) Assignees: NYZ AB, Helsingborg (SE); WM17 HOLDING AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/734,509

(22) Filed: Jun. 9, 2015

(65) Prior Publication Data

US 2015/0272878 A1    Oct. 1, 2015

Related U.S. Application Data

(63) Continuation of application No. 14/008,367, filed as application No. PCT/SE2012/050336 on Mar. 28, 2012.

(60) Provisional application No. 61/470,264, filed on Mar. 31, 2011.

(30) Foreign Application Priority Data

Mar. 29, 2011    (SE) ..................... 1150273

(51) Int. Cl.

| A61K 9/00 | (2006.01) |
|---|---|
| A61K 47/38 | (2006.01) |
| A24B 15/16 | (2006.01) |
| A61K 9/14 | (2006.01) |
| A61K 9/16 | (2006.01) |
| A61K 31/465 | (2006.01) |
| A61K 47/12 | (2006.01) |
| A61K 47/22 | (2006.01) |
| A61K 47/26 | (2006.01) |
| A61K 47/32 | (2006.01) |

(52) U.S. Cl.
CPC ............... *A61K 9/0056* (2013.01); *A24B 15/16* (2013.01); *A61K 9/006* (2013.01); *A61K 9/009* (2013.01); *A61K 9/145* (2013.01); *A61K 9/1611* (2013.01); *A61K 9/1623* (2013.01); *A61K 9/1635* (2013.01); *A61K 9/1652* (2013.01); *A61K 31/465* (2013.01); *A61K 47/12* (2013.01); *A61K 47/22* (2013.01); *A61K 47/26* (2013.01); *A61K 47/32* (2013.01); *A61K 47/38* (2013.01)

(58) Field of Classification Search
CPC ....... A61K 31/465; A61K 9/009; A24B 15/16
See application file for complete search history.

(56) References Cited

U.S. PATENT DOCUMENTS

| 8,529,914 B2 | 9/2013 | Fuisz et al. |
| 2005/0053665 A1 | 3/2005 | Ek et al. |
| 2005/0061339 A1 | 3/2005 | Hansson et al. |
| 2006/0147498 A1 | 7/2006 | Jonsson et al. |
| 2008/0138423 A1 | 6/2008 | Gonda |
| 2009/0293895 A1 | 12/2009 | Axelsson et al. |
| 2011/0268809 A1 | 11/2011 | Brinkley et al. |

FOREIGN PATENT DOCUMENTS

| FR | 2792200 | 10/2000 |
| WO | WO 92/01445 | 2/1992 |
| WO | WO 03/039518 | 5/2003 |
| WO | WO 2004/056363 | 7/2004 |
| WO | WO 2004/064811 | 8/2004 |
| WO | WO 2010/104464 | 9/2010 |

OTHER PUBLICATIONS

International Search Report for International Application No. PCT/SE2010/050336 mailed May 11, 2012 (4 pages).

Extended European Search Report for EP Application No. 12765290.7 mailed Aug. 13, 2014 (5 pages).

Thornley et al. "A single-blind, randomized, crossover trial of the effects of a nicotine pouch on the relief of tobacco withdrawal symptoms and user satisfaction," Nicotine & Tobacco Research, vol. 11, No. 6 (Jun. 2009); 715-721.

*Primary Examiner* — Gina Justice (74) *Attorney, Agent, or Firm* — Merchant & Gould P.C.

(57) ABSTRACT

The invention relates to a product for oral delivery of nicotine containing a core comprising a powder of at least one free nicotine salt, at least one pH adjusting agent and at least one filler, and a water insoluble pouch, wherein said pouch is permeable for saliva and therein dissolved parts of the powder, wherein said product upon contact with purified water gives a pH of at least 6. The invention also relates to a method to manufacture such a product.

19 Claims, 2 Drawing Sheets

POUCH CONTAINING NICOTINE IN FREE SALT FORM

CLAIM OF PRIORITY

This application is a Continuation of U.S. Ser. No. 14/008,367, filed 27 Sep. 2013, now U.S. Pat. No. 9,161,908, which is a National Stage Application of PCT/SE2012/050336, filed 28 Mar. 2012, which claims the benefit of Serial No. 1150273-9, filed 29 Mar. 2011 in Sweden and Ser. No. 61/470,264, filed 31 Mar. 2011 in the United States and which applications are incorporated herein by reference. To the extent appropriate, a claim of priority is made to each of the above disclosed applications.

FIELD OF INVENTION

The invention relates to a product for oral delivery of nicotine containing a core comprising a powder of at least one free nicotine salt, at least one pH adjusting agent and at least one filler, and a water insoluble pouch, wherein said pouch is permeable for saliva and therein dissolved parts of the powder, wherein said product upon contact with purified water gives a pH of at least 6. The invention also relates to a method to manufacture such a product.

BACKGROUND ART

Smoking articles, (e.g. cigarettes and cigars) are made from tobacco. The administration of nicotine from tobacco by smoking provides satisfaction. Smoking is however associated with health hazards which are not necessarily related to the administration of nicotine itself. Important risk factors are substances which are formed or released during the combustion of tobacco, such as carcinogenic nitrosamines, carbon monoxide and tar products.

As smoking of tobacco has health hazards it is desirable to formulate alternative means of administering nicotine in a pleasurable manner to facilitate reduction of or cessation from smoking. Nicotine is a strongly addictive substance and it is generally accepted that the difficulty to quit smoking results from the fact that smokers are dependent upon nicotine. It is therefore desirable to be able to provide nicotine with a low amount of other potential hazardous components. Prior art has suggested, as an alternative to smoking, a number of different nicotine administration forms such as gum, patch, nasal spray, lozenge and oral pouch.

When smoking a cigarette, nicotine is almost immediately absorbed into the smoker's blood and quickly reaches the brain. The quick uptake gives the smoker rapid satisfaction. Therefore, in the treatment with nicotine-containing products a rapid uptake of nicotine is desirable. It is therefore desirable to provide a nicotine product which rapidly delivers nicotine to the user and thereby provides the user with the desired effect.

It is also desirable to provide a nicotine product which gives an almost complete delivery of the nicotine to the user to avoid unnecessary waste.

Nicotine base is readily oxidized and formulations containing nicotine base may have problem with the volatility of nicotine. A number of different formulations where the nicotine base has formed a combination with other components have been developed to deal with the stability and volatility problems of nicotine base. Nicotine base has for example been bound to, adsorbed to, absorbed into, enclosed into or forming a complex or any other non-covalent bounding with other components, such as starch, alginate salts, beta-cyclodextrin and cellulose.

WO 2010/104464 A1 describes a matrix of alginate salt which entraps a biological active substance, such as nicotine within the matrix. The nicotine, which can be provided as a nicotine salt, is dissolved in an aqueous solution together with the alginate salt and other components, such as buffer components. When the solution is dried, the nicotine will, together with other dissolved components, be entrapped within the alginate matrix. The matrix will provide a protection for the nicotine and may also be used to regulate the nicotine delivery from the matrix.

US 2005/0053665 A1 describes nicotine which is absorbed into or adsorbed to cellulose of non-seed origin. This cellulose provides a high internal and external surface. In this way a high concentration of liquid free nicotine base, or other liquid, semisolid or solid form of nicotine are transferred to chemically stable, solid products. In the products, nicotine prevails in a readily bioavailable and unionized base form.

WO 92/01445 describes an osmotic device consisting of a compartment, such as a solid mass or a tablet, which is enclosed into a wall which is permeable to an aqueous fluid. The compartment contains nicotine salt and other components which initiate a chemical reaction between the nicotine salt and the aqueous fluid to produce nicotine base. The wall is not permeable for the nicotine base but the nicotine base is delivered from the compartment through a passageway in the wall. The release of nicotine base from the product can continue for several hours.

A rapid nicotine release rate has normally not been the major concern for nicotine combinations and in many cases the approach has resulted in a rather moderate release rate of nicotine. Further, a nicotine combination or an osmotic device requires a rather intricate manufacturing method. It is therefore desirable to provide a nicotine formulation with a satisfactory chemical stability and low volatility of the nicotine component without compromising the demands for a rapid nicotine delivery and a simple manufacturing method.

"Snus" or snuff is a tobacco mixture from which the consumer forms a portion and places it under the upper lip. Alternatively, the tobacco mixture is already preportioned into pouches which are placed under the upper lip. The use of "snus" normally results in nicotine blood levels with a rather high steady state nicotine blood concentration, but they do not provide the peak levels obtained from smoking. The reason for this is that nicotine is released too slowly from the "snus" product.

Further, "snus" normally deliver only a fraction of the available nicotine to the user. After 30 minutes use, for a number of "snus" products, the delivery of nicotine is often less than 50%, for some products less than 25% of the available amount of nicotine.

A nicotine product similar to tobacco "snus" pouches, but with a purer source of nicotine than tobacco, and a faster and more complete release of nicotine could be an important aid in smoke reduction or cessation.

To summarize, it is desirable to provide an improved product for reduction of or cessation from smoking. A product similar to tobacco "snus" pouches, but without the disadvantages associated with tobacco "snus" pouches, could be an attractive option. The product should give a rapid and almost complete delivery of nicotine, be free from other harmful components, deal with the stability and volatility problems of nicotine base and finally be cheap and simple to manufacture.

SUMMARY OF THE INVENTION

The invention relates to a product for oral delivery of nicotine containing a core comprising a powder of at least one free nicotine salt, at least one pH adjusting agent and at least one filler, and a water insoluble pouch, wherein said pouch is permeable for saliva and therein dissolved parts of the powder, wherein said dosage form upon contact with purified water give a pH of at least 6. The invention also relates to a method to manufacture such a product.

Nicotine is generally in either base form or in salt form. Nicotine base is readily absorbed through mucosal membranes. Unfortunately, nicotine base is highly unstable and is difficult to contain using conventional packaging materials. Nicotine salts, on the other hand, are generally stable. Nicotine salts, however, are not readily absorbed through mucosal membranes. While the shelf life and packaging problems could be overcomed by incorporating a nicotine salt into the product, such a product would have had an undesirably low nicotine absorption rate through the mucosal membranes. This problem can be solved by incorporating a pH adjusting agent which converts the nicotine salt into nicotine base in situ.

Many nicotine salts are known to be physically and chemically stable. By using a suitable pharmaceutically acceptable nicotine salt, instead of nicotine base, the problems with the oxidation and the volatility can be reduced or avoided. By using a nicotine salt it is not necessary to form a combination between the nicotine and other components in the powder to protect the nicotine from oxidation and high volatility. The nicotine salt can be free, i.e. it only needs to be mixed together with the other components in the powder. Further, the nicotine salt shall be reasonably water soluble in order to obtain a rapid dissolution of the nicotine salt in an aqueous liquid, such as the saliva in the oral cavity. For a person skilled in the art suitable nicotine salts possessing these properties can easily be selected.

The powder also contains one or more pH adjusting agents. These ensure that when the powder is dissolved in saliva, a sufficiently high local pH is obtained. Such a high local pH is important to ensure that the dissolved nicotine is unprotonated and hence can be effectively absorbed through the oral mucosa.

In some embodiments it might be that the nicotine salts and pH adjusting agents need to be separated from each other during storage of the product. A high pH can have a negative effect on the stability of an otherwise stable nicotine salt. In these cases the pH adjusting agent may be encapsulated or embedded for example with a polymer before mixing it with the nicotine salt thus physically separating it from the nicotine salt during storage.

The powder also contains one or more fillers to ensure that the amount of powder in a unit dose is suitable. Fillers can also have a secondary function such as being for example a sweetener or a flavor.

The powder described above is contained in a water insoluble pouch which prevents the powder particles to leave the pouch. The pouch is permeable to aqueous liquids such as saliva. This means that in operation, saliva present in the oral cavity can penetrate through the pouch, dissolve the nicotine salt and the pH adjusting agent in the core, and thereafter transport the dissolved substances out through the pouch into the oral cavity. A reaction between the pH adjusting agent and the nicotine salt results in the formation of unprotonated nicotine. The ratio between unprotonated and protonated nicotine depends on the local pH. Once in the oral cavity, the nicotine can be absorbed through the mucosal membrane.

In a second aspect the invention relates to a method to produce such a product comprising the steps of providing the components used in the powder and mixing the components. If needed, the pH adjusting agent may be encapsulated or embedded with a polymer. A drying step may be necessary if any of the added components is a liquid. Depending on the desired properties, the powder mixture may or may not be granulated. If liquid components are added to the powder during manufacture it is important to ensure that the liquid components do not, to a significant extent, dissolve the nicotine salt as this may result in a lower chemical stability. The powder is thereafter positioned inside the pouch which is sealed.

It is for the first time possible to obtain a product comprising a powder mixture with a free nicotine salt that gives a rapid and almost complete delivery of nicotine which becomes available for the consumer, is free from other harmful components, deals with the stability and volatility problems and finally is cheap and simple to manufacture. With the product the consumer will get a faster satisfaction compared to several other products available on the market today, such as nicotine gums.

BRIEF DESCRIPTION OF THE DRAWINGS

In the two figures below, the nicotine release from products according to the disclosed invention as well as reference products are presented.

DETAILED DESCRIPTION OF THE INVENTION

Definitions

The term "free" nicotine salt is intended to mean that the nicotine salt in the product during storage, before use by the consumer, does not form any combination with any other component in the product. By providing the nicotine as a suitable salt, the nicotine source is not volatile or prone of oxidation and thereby stable during storage eliminating the need for a combination.

The term "pH adjusting agent" is intended to mean one or more substances added with the purpose to adjust and control the pH of an aqueous liquid, such as saliva, when the product containing the pH adjusting agent is dissolved or dispersed in said aqueous liquid.

The term "encapsulated or embedded pH adjusting agent" is intended to mean a pH adjusting agent which has been encapsulated or embedded in order to physically separate it from the nicotine salt and thereby give a product which is chemically stable over its intended storage time.

The term "local pH" is intended to mean the pH in an aqueous liquid in close proximity to the product, such as the pH in saliva in close proximity to the product in use.

The term "filler" is intended to mean a material that increase the volume of the powder. In one embodiment the filler is present to increase the volume of pouches to be used under the lip. A filler can also have a secondary function such as being a sweetener or a flavor.

The term "physically and chemically stable" nicotine salt is intended to mean a nicotine salt which is physically and chemically stable over its intended storage time.

The term "water soluble" nicotine salt is intended to mean a nicotine salt which has an aqueous solubility which adequate for its intended use. A high water solubility often also implies a high rate of dissolution in an aqueous liquid.

The term "pharmaceutically acceptable" is intended to mean a non-toxic material that does not decrease the effectiveness of the biological activity of the active ingredients, i.e. the nicotine. Such pharmaceutically acceptable excipients are well-known in the art (see for example Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

Product

The invention relates to a product for oral delivery of nicotine containing a core comprising a powder of one or more free nicotine salts, one or more pH adjusting agents, one or more fillers, and a water insoluble pouch, wherein said pouch is permeable for saliva and therein dissolved parts of the powder, wherein said product upon contact with purified water give a pH of at least 6.

If the product shall be able to deliver nicotine rapidly and almost completely to the oral cavity under normal user conditions the following demands must be fulfilled.

Firstly, the powder must of course be formulated to release nicotine when subjected to an aqueous liquid. A formulation where the nicotine is tightly bound in for example a complex, or a formulation comprising a nicotine salt with a very low aqueous solubility may have an unsatisfactory release of nicotine also in the presence of large amounts of aqueous liquid. It is obvious that formulations with such intrinsic low release rate of nicotine have unsatisfactory nicotine release rates in the oral cavity under normal user conditions.

Secondly, the formulation must have a satisfactory nicotine release also when the amount of aqueous liquid, such as saliva in the oral cavity, is limited. Different formulations may have different demands on the amounts of aqueous liquid needed for a rapid and almost complete delivery of nicotine. Certain formulations, which may release nicotine rapidly in the presence of large amounts of an aqueous liquid, may not satisfactorily deliver nicotine in the oral cavity under normal user conditions as the amount of saliva available is too limited.

Thirdly, the pouch must have a suitable design and be made of a material which allows an easy flow of saliva into the pouch and an easy flow of saliva and therein dissolved parts of the powder out of the pouch.

Nicotine base is readily oxidized and formulations with nicotine base may have problem with the volatility of nicotine. On the other hand, many nicotine salts are known to be chemically stable. By using a suitable pharmaceutically acceptable nicotine salt, instead of nicotine base, the problems with the oxidation and the volatility of nicotine can be avoided. By using a physically and chemically stable nicotine salt it is not necessary to form a combination with other component in the product in order to improve the storage stability i.e. the nicotine salt can be free.

The nicotine salt shall be reasonably water soluble in order to obtain a rapid and complete dissolution in the limited amount of saliva entering into the core when the product is used. The saliva is entering the core through the pouch, dissolves the nicotine salt, and the dissolved nicotine is transported out of the core, through the pouch, with the saliva.

For a person skilled in the art suitable nicotine salts possessing these properties can easily be selected. Examples of suitable nicotine salts are nicotine hydrochloride, nicotine dihydrochloride, nicotine monotartrate, nicotine bitartrate, nicotine bitartrate dihydrate, nicotine sulphate, nicotine zinc chloride monohydrate and nicotine salicylate, and mixtures thereof. In particular, nicotine bitartrate dihydrate is suitable for use in the powder of the invention.

The amount of nicotine salt in one portion may be from 0.1 mg to 10 mg of nicotine calculated as nicotine base ($C_{10}H_4N_2$, CAS no. 54-11-5) such as 0.5, 1.0, 1.5, 2.0, 2.5, 3.0, 3.5, 4.0, 4.5, 5.0, 6.0, 7.0, 8.0 or 9.0 mg of nicotine.

The pH adjusting agents shall be a pharmaceutically acceptable and provide a pH of 6 or above when the powder in the product is dissolved or dispersed in purified water. Examples of such pH adjusting agents are carbonates including monocarbonate, bicarbonate and sesquicarbonate, acetates, glycinates, gluconates, borates, glycerophosphates or citrates of alkaline metals or ammonium, phosphate systems including monohydrogenphosphate, dihydrogenphosphate and trihydrogenphosphate, metal hydroxides such as sodium hydroxide and potassium hydroxide, and mixtures thereof. One example of a suitable pH adjusting system is sodium bicarbonate and sodium carbonate, and mixtures thereof.

In some embodiments it might be that the nicotine salts and pH adjusting agents in the product need to be separated from each other during storage. A high pH can have a negative effect on the stability of the otherwise stable nicotine salt. In these cases the pH adjusting agent may be encapsulated or embedded for example with a polymer before mixing it with the other components. Such encapsulating or embedding will protect the nicotine salt from the alkaline components in the pH adjusting agent. The nicotine salt and the pH adjusting agent will mix only, during use, when the saliva is dissolving and releasing the components into the oral cavity.

Absorption of nicotine from the oral cavity, i.e. transmucosal uptake, to the systemic circulation is dependent on the local pH of the saliva inside and close to the product in use. Nicotine will predominantly be absorbed through the mucosa in the nonprotonated form. Therefore, it is preferable with a local pH which results in a high fraction of the nonprotonated nicotine. The pKa of nicotine is about 7.8 which means, for example, that at a pH of about 8.8 approximately 90% of the nicotine is in the nonprotonated form. By pH adjusting, the local pH of the saliva can be increased and therefore the absorption of nicotine is increased compared to if no pH adjustment was performed. Theoretically, the higher the local pH, the higher the fraction of nonprotonated nicotine. However, a too high pH will be irritating for the oral mucosa. Therefore taking the above mentioned aspects into account, a practical upper limit of the pH may be for example about pH 10.

The pH adjusting agents adjust the pH to above 6 when the powder is dissolved or dispersed in purified water. For example, it may be desirable to obtain a pH of about 8.5 such as 7.5 to 9.5.

Thereby the nicotine salt in the powder is in a physical and chemical stable form until the product is used by a consumer and comes into contact with saliva. Saliva present in the oral cavity penetrate through the pouch, dissolve the nicotine salt and the pH adjusting agent in the core, and thereafter transport the dissolved substances out through the pouch into the oral cavity. A reaction between the pH adjusting agent and the nicotine salt in the saliva results in the formation of unprotonated nicotine which can penetrate the oral mucosa and become absorbed.

The product also contains one or more fillers. The filler increases the volume of pouches. For example, if a pouch is too small it may stick to the lip and be difficult to remove after use. Examples of fillers include polysaccharides, polyols, sugars, natural fibres, microcrystalline cellulose, cellulose and cellulose derivatives, and mixtures thereof. The filler may also have a secondary function, such as for example as sweetener or flavour.

Fillers with a secondary function may give the powder improved properties when it comes to the manufacture of the product or the experience of the powder and the effects of the powder on the consumer. The type of components and the amount of the different components in the powder may vary depending on the desired properties of the final product, for example to obtain an attractive taste or a good power flow. Typically, the mixture may comprise one or more fillers having a function as sweetener or flavour.

Compared to tobacco based products, the powder mixture is free from nitrosamines as well as other potential hazardous components which normally can be found in tobacco.

Examples of sweeteners include mono- di- tri- and polysaccharides, polyols such as mannitol, maltitol and xylitol, natural and synthetic sweeteners such as sucrose, glucose, dextrose, maltose, fructose, saccharin, aspartame, acesulfame, sucralose, saccharin and cyclamates, and mixtures thereof.

Examples of flavors include bergamot, eucalyptus, orange, mandarin, citrus, lemon, peppermint, mint, menthol, liquorice, wintergreen, tobacco, coffee, vanilla, lime, apple, peach and mixtures thereof.

The powder may, or may not, be granulated. A granulation may increase the particle size of the powder which can for example decrease the dustiness or improve the powder flow. An example of a granulating agent is polyvinylpyrrolidine such as Kollidon 25.

Other examples of excipients are well-known in the art and can be found in Handbook of Pharmaceutical Excipients edited by Rowe, R. C. et al., 4.sup.th edition, Pharmaceutical Press, London 2003, which is hereby incorporated by reference.

The powder is filled into pouches and is maintained in the pouch by a sealing. An ideal pouch shall have the following characteristics: it shall be chemically and physically stable, be pharmaceutically acceptable, be insoluble in water, be easy to fill with powder and seal and it shall provide a semipermeable membrane layer which prevent the powder from leaving the bag but permit saliva and therein dissolved components from the powder in the pouch, such as nicotine, to freely pass through said pouch.

The pouch material may be of any suitable material e.g. woven or non-woven fabric (e.g. cotton, fleece etc.), heat sealable non-woven cellulose or other polymeric material such as synthetic, semi-synthetic or natural polymeric material. An example of suitable pouch material is paper made of pulp and a small amount of wet strength agent.

The pouch is placed in the oral cavity by the user. Saliva enters into the pouch, and nicotine and other components which are soluble in saliva start to dissolve and are transported with the saliva out of the pouch into the oral cavity where the nicotine is absorbed.

The product may comprise from 50 to 1000 mg of said powder, such as 100, 150, 200, 250, 300, 350, 400, 450, 500, 550, 600, 650, 700, 750, 800, 850, 900 or 950 mg.

Method

The invention also relates to a method of manufacturing the product according to the invention.

The manufacture of the powder in the core comprise the steps of providing powders of at least one free nicotine salt, at least one pH adjusting agent and at least one filler and mixing the components. The mixing may be performed in a conventional blender. One or more sieving steps may be advantageous to improve the blending homogeneity.

If needed, the pH adjusting agent may be encapsulated or embedded with for example a polymer before mixing with the nicotine salt. This can be performed by adding a polymer solution to the pH adjusting agent and thereafter evaporate the solvent to form a powder consisting of the pH adjusting agent encapsulated or embedded with the polymer.

If any of the components is a liquid additional manufacturing steps may be needed. Typically, several flavors are liquids or liquid solutions and then there may be a need of a drying step. Further, depending on the desired properties the powder may be granulated, or not. If the powder mixture shall be granulated, for example to improve the powder flow properties, a granulating step is added. If, optionally, liquid components are added to the powder during manufacture it is important to ensure that the liquid components do not, to a significant extent, dissolve the nicotine salt as this may result in a lower chemical stability. Finally, the powder is positioned inside the pouch which is sealed.

By such a simple and controlled way of manufacturing the product it is possible in a cheap and simple way to obtain an effective product with excellent storage stability.

EXAMPLES

The following examples are illustrative of the present invention and should not be considered as limiting the scope of the invention. A person skilled in the art, in light of the present disclosure, appreciate that many changes can be made in the specific embodiments which are disclosed and still obtain a like or similar result without departing from the spirit and the scope of the invention.

In Examples 1 to 8, a number of compositions according to the disclosed invention are presented and the manufacturing processes are described. In Example 1 powder mixtures are presented, in Examples 2 to 8 granulated batches are presented (including Examples 7 and 8 where the pH adjusting agent has been encapsulated with a polymer).

In Example 9 pH measurements are presented, in Example 10 nicotine release rates are presented, and in Example 11 the stability during storage is presented for a number of batches.

Example 1

A number of compositions according to the disclosed invention are presented in Table 1.

TABLE 1

| | Compositions according to the disclosed invention (mg per pouch). | | | | | | | | |
|---|---|---|---|---|---|---|---|---|---|
| | A | B | C | F | G | I | J | K | L |
| Nicotine bitartrate dihydrate | 3.1 (*) | 3.1 | 3.1 | 9.2 () | 9.2 | 9.2 | 15.4 (*) | 15.4 | 15.4 |
| Maltitol | 220.9 | — | — | 119.8 | 118.9 | 108.9 | 104.3 | — | 479.3 |

TABLE 1-continued

Compositions according to the disclosed invention (mg per pouch).

| | A | B | C | F | G | I | J | K | L |
|---|---|---|---|---|---|---|---|---|---|
| Mannitol | — | 220.9 | — | — | — | — | 104.3 | 229.3 | — |
| Avicel PH 200 | — | — | 20.9 | 95.0 | 95.0 | 95.0 | — | 229.3 | 479.3 |
| Sodium bicarbonate | 21.0 | 21.0 | 21.0 | 16.5 | 16.5 | 16.5 | 11.5 | 11.5 | 11.5 |
| Sodium carbonate | 5.0 | 5.0 | 5.0 | 9.5 | 9.5 | 9.5 | 14.5 | 14.5 | 14.5 |
| Acesulfame K | — | — | — | — | 0.9 | 0.9 | — | — | — |
| Menthol Durarome | — | — | — | — | — | 10 | — | — | — |
| TARGET FILL WEIGHT | 250 | 250 | 50 | 250 | 250 | 250 | 250 | 500 | 1000 |

(*) Corresponds to nicotine base 1 mg per pouch
(**) Corresponds to nicotine base 3 mg per pouch
(***) Corresponds to nicotine base 5 mg per pouch Products with compositions according to Table 1 are manufactured in the following way: The components are provided as powders. The powders are mixed and sieved to form powder mixtures. The powder mixtures are manually filled into pouches. The target fill weights per pouch are presented in Table 1. The pouch is made from long fiber paper.

Example 2

10.0 g Kollidon 25 (polyvinylpyrrolidone) is dissolved in 18.0 g ethanol. 13.0 g Lemon Flavor (Firmenich), 2.5 g glycerol and 0.5 g menthol are added to form a homogeneous granulation solution.

The following solid components are mixed and sieved to form a powder mixture: 12.3 g nicotine bitartrate dihydrate, 185.3 g mannitol, 0.4 g Acesulfame K, 16.0 g sodium bicarbonate and 10.0 g sodium carbonate.

The granulation solution is slowly added to the powder mixture under stirring. The granulate is sieved and placed on a tray. The powder is dried at 60° C. over night and is thereafter sieved.

The powder is manually filled into pouches (target fill weight 250 mg powder per pouch). The pouch is made from long fiber paper.

Example 3

70.0 g Kollidon 25 is dissolved in 105.0 g ethanol. 17.5 g Lemon Flavor (Firmenich), 7.0 g Fresh Peppermint Flavor (Firmenich), 3.5 g Mandarin Flavor (Firmenich) and 1.4 g menthol are added to form a homogeneous granulation solution.

The following solid components are mixed in a planetary mixer and further blended by sieving to form a powder mixture: 43.0 g nicotine bitartrate dihydrate, 192.5 g Avicel PH200, 447.3 g mannitol, 1.8 g Acesulfame K, 56.0 g sodium bicarbonate and 35.0 g sodium carbonate.

The granulation solution is slowly added to the powder mixture under stirring in a planetary mixer. The granulate is sieved and placed on a tray. The powder is dried at ambient conditions over night and is thereafter sieved.

The powder is filled into pouches (target fill weight 250 mg powder per pouch) using an in-house pouch filling machine. The pouch is made from long fiber paper.

Example 4

70.0 g Kollidon 25 is dissolved in 105.0 g ethanol. 21.0 g Lemon Flavor (Firmenich), 8.4 g Fresh Peppermint Flavor (Firmenich), 4.2 g Mandarin Flavor (Firmenich) and 1.8 g menthol are added to form a homogeneous granulation solution.

The following solid components are mixed in a planetary mixer and further blended by sieving to form a powder mixture: 43.0 g nicotine bitartrate dihydrate, 385.0 g Avicel PH200, 248.5 g maltitol, 2.3 g Acesulfame K, 56.0 g sodium bicarbonate and 35.0 g sodium carbonate.

The granulation solution is slowly added to the powder mixture under stirring in a planetary mixer. Additional 20 g of ethanol is added after the addition of the granulation liquid. The granulate is sieved and placed on a tray. The powder is dried at ambient conditions over night and is thereafter sieved.

The powder is filled into pouches (target fill weight 250 mg powder per pouch) using an in-house pouch filling machine. The pouch is made from long fiber paper Example 5

70.0 g Kollidon 25 is dissolved in 105.0 g ethanol. 21.0 g Lemon Flavor (Firmenich), 8.4 g Fresh Peppermint Flavor (Firmenich) and 4.2 g Mandarin Flavor (Firmenich) are added to form a homogeneous granulation solution.

The following solid components are mixed in a planetary mixer and further blended by sieving to form a powder mixture: 43.0 g nicotine bitartrate dihydrate, 385.0 g Avicel PH200, 236.3 g maltitol, 2.3 g Acesulfame K, 56.0 g sodium bicarbonate, 35.0 g sodium carbonate and 14.0 g Menthol Durarome.

The granulation solution is slowly added to the powder mixture under stirring in a planetary mixer. Additional 10 g of ethanol is added after the addition of the granulation liquid. The granulate is sieved and placed on a tray. The powder is dried at ambient conditions over night and is thereafter sieved.

The powder is filled into pouches (target fill weight 250 mg powder per pouch) using an in-house pouch filling machine. The pouch is made from long fiber paper.

Example 6

70.0 g Kollidon 25 is dissolved in 105.0 g ethanol. 21.0 g Lemon Flavor (Firmenich), 8.4 g Fresh Peppermint Flavor (Firmenich) and 4.2 g Mandarin Flavor (Firmenich) are added to form a homogeneous granulation solution.

The following solid components are mixed in a planetary mixer and further blended by sieving to form a powder mixture: 21.5 g nicotine bitartrate dihydrate, 385.0 g Avicel PH200, 257.6 g maltitol, 2.3 g Acesulfame K, 73.5 g sodium bicarbonate, 17.5 g sodium carbonate and 14.0 g Menthol Durarome The granulation solution is slowly added to the powder mixture under stirring in a planetary mixer. Additional 10 g of ethanol is added after the addition of the granulation liquid. The granulate is sieved and placed on a tray. The powder is dried at ambient conditions over night and is thereafter sieved.

The powder is filled into pouches (target fill weight 250 mg powder per pouch) using an in-house pouch filling machine. The pouch is made from long fiber paper.

Example 7

Encapsulated pH adjusting agent is manufactured in the following way: 480.0 g sodium bicarbonate and 300.0 g sodium carbonate are mixed. 60.0 g Eudragit L100 is dissolved in 342 g ethanol. The granulation solution is slowly added to the powder mixture under stirring in a planetary mixer. The granulate is sieved and placed on a tray. The powder is dried at ambient conditions over night and is thereafter sieved.

Example 8

70.0 g Kollidon 25 is dissolved in 80.0 g ethanol. 21.0 g Lemon Flavor (Firmenich), 8.4 g Fresh Peppermint Flavor (Firmenich) and 4.2 g Mandarin Flavor (Firmenich) are added to form a homogeneous granulation solution.

The following solid components are mixed in a planetary mixer and further blended by sieving to form a powder mixture: 43.0 g nicotine bitartrate dihydrate, 385.0 g Avicel PH200, 229.3 g maltitol, 2.3 g Acesulfame K and 14.0 g Menthol Durarome The granulation solution is slowly added to the powder mixture under stirring in a planetary mixer. The granulate is sieved and placed on a tray. The powder is dried at ambient conditions over night and is thereafter sieved.

The obtained granulate is mixed with Encapsulated pH adjusting agent (described in Example 7). For one part of granulated powder, 0.126 parts of Encapsulated pH adjusting agent is added.

The mixed powder is filled into pouches (target fill weight 250 mg powder per pouch) using an in-house pouch filling machine. The pouch is made from long fiber paper.

The compositions of the nicotine pouches manufactured according to Examples 2 to 8 above are summarized in Table 2.

TABLE 2

Compositions of the formulations in Examples 2 to 8 (mg per pouch)

|  | 2 | 3 | 4 | 5 | 6 | 7 | 8 |
|---|---|---|---|---|---|---|---|
| Nicotine bitartrate dihydrate | 12.3 (*) | 12.3 | 12.3 | 12.3 | 6.15 (**) | 12.3 | 12.3 |
| Mannitol | 185 | 128 | — | — | — | — | — |
| Maltitol | — | — | 71.0 | 67.5 | 73.6 | 65.5 | 65.5 |
| Avicel PH 200 | — | 55.0 | 110 | 110 | 110 | 110 | 110 |
| Sodium bicarbonate | 16.0 | 16.0 | 16.0 | 16.0 | 16.0 | — | — |
| Sodium carbonate | 10.0 | 10.0 | 10.0 | 10.0 | 10.0 | — | — |
| Encapsulated pH adjusting agent (***) | — | — | — | — | — | 28.0 | 28.0 |
| Acesulfame K | 0.40 | 0.50 | 0.65 | 0.65 | 0.65 | 0.65 | 0.65 |
| Glycerol | 2.50 | — | — | — | — | — | — |
| Lemon flavour | 13.0 | 5.00 | 6.00 | 6.00 | 6.00 | 6.00 | 6.00 |
| Fresh peppennint flavour | — | 2.00 | 2.40 | 2.40 | 2.40 | 2.40 | 2.40 |
| Mandarin flavour | — | 1.00 | 1.20 | 1.20 | 1.20 | 1.20 | 1.20 |
| Menthol | 0.50 | 0.40 | 0.50 | — | — | — | — |
| Menthol Durarome | — | — | — | 4.00 | 4.00 | 4.00 | 4.00 |
| Kollidon PVP25 | 10.0 | 20.0 | 20.0 | 20.0 | 20.0 | 20.0 | 20.0 |

(*) Corresponds to nicotine base 4 mg per pouch
(**) Corresponds to nicotine base 2 mg per pouch
(***) 16.0 mg Sodium bicarbonate, 10.0 mg Sodium carbonate and 2.0 mg Eudragit L100

70.0 g Kollidon 25 is dissolved in 105.0 g ethanol. 21.0 g Lemon Flavor (Firmenich), 8.4 g Fresh Peppermint Flavor (Firmenich) and 4.2 g Mandarin Flavor (Firmenich) are added to form a homogeneous granulation solution.

The following solid components are mixed in a planetary mixer and further blended by sieving to form a powder mixture: 43.0 g nicotine bitartrate dihydrate, 385.0 g Avicel PH200, 229.3 g maltitol, 2.3 g Acesulfame K, 98.0 g Encapsulated pH adjusting agent and 14.0 g Menthol Durarome.

The granulation solution is slowly added to the powder mixture under stirring in a planetary mixer. The granulate is sieved and placed on a tray. The powder is dried at ambient conditions over night and is thereafter sieved.

The powder is filled into pouches (target fill weight 250 mg powder per pouch) using an in-house pouch filling machine. The pouch is made from long fiber paper.

Example 9

The pH is determined for products according to the disclosed invention. A pouch is added to 15.0 g purified water. The sample is stirred or shaken and after at least 30 minutes the pH is measured using a conventional pH meter. The investigated products are described in the Examples above.

TABLE 3 pH for products according to the disclosed invention

|  | pH |
|---|---|
| 1F | 9.0, 9.0 |
| 1I | 8.9, 9.1 |
| 3 | 8.46, 8.52, 8.47, 8.46 |

TABLE 3-continued pH for products according
to the disclosed invention

| | pH |
|---|---|
| 4 | 8.63, 8.62 |
| 6 | 8.44, 8.53 |
| 7 | 8.34 |
| 8 | 8.14 |

It is seen that the pH for the investigated products is above pH 6.

Example 10

The release of nicotine from products according to the disclosed invention is presented. As a reference, the release of nicotine from products not according to the disclosed invention, determined with the same methods, is also presented.

Investigated Samples

The products according to the disclosed invention are described in Examples 1 to 8 and in Tables 1 and 2.

The two reference products manufactured from nicotine containing powders filled into a pouches are also tested. The nicotine source is however not a nicotine salt as in the disclosed invention, but nicotine combinations.

The first reference product is a commercially available product, "Zonnic mint 4 mg" purchased in Sweden. Three batches of Zonnic have been investigated. The formulation is based upon a nicotine-cellulose combination and contains 4 mg nicotine per pouch. WO 2007/104573 and WO 2010/031552 relate to said nicotine-cellulose combination for the preparation of a nicotine pouch composition. In the patent applications it is stated that a nicotine-cellulose combination is specially suitable for use in snuff compositions, as such a snuff composition on one hand releases nicotine relatively fast and thereby enables a fast onset of nicotine effect, and on the other hand enables the nicotine content to be completely or almost completely released after application to the oral cavity. It is therefore of interest to compare the nicotine release from products according to the disclosed invention with the nicotine release for a product according to the invention described in WO 2007/104573 and WO 2010/031552.

The second reference product is based on a nicotine polacrilex complex (Amberlite IRP 64). This complex is commercially available and is used in nicotine products for smoking reduction and cessation. It was purchased from Cambrex, and contains 15% nicotine. In Table 4, the compositions for two reference batches based upon the nicotine polacrilex complex are presented (R1 and R2). Both batches were manufactured in house in a similar way as described in Examples 2-6 with the important exception that a nicotine complex, and not a nicotine salt, was used.

TABLE 4

Compositions of the reference product
based upon a nicotine polacrilex
complex (mg per pouch)

| | 10R1 | 10R2 |
|---|---|---|
| Nicotine polacrilex | 42.0 (*) | 42.0 |
| Ascorbyl palmitate | 4.0 | 4.0 |
| Mannitol | 152 | 122 |
| Avicel PH 200 | — | 30.0 |
| Sodium bicarbonate | 15.0 | 15.0 |
| Sodium carbonate | 9.00 | 9.00 |

TABLE 4-continued

Compositions of the reference product
based upon a nicotine polacrilex
complex (mg per pouch)

| | 10R1 | 10R2 |
|---|---|---|
| Acesulfame K | 0.30 | 0.30 |
| Glycerol | 2.50 | 2.50 |
| Lemon flavour | 12.0 | 12.0 |
| Menthol | 0.50 | 0.50 |
| Kollidon PVP25 | 15.0 | 15.0 |

(*) Corresponds to 6.3 mg nicotine base per pouch

Experimental Methods

A nicotine pouch is normally placed under the upper lip where only a limited amount of saliva is available to release the nicotine. Therefore when trying to mimic the nicotine release rate in vitro it is an advantage to use experimental conditions where only a limited amount of aqueous liquid is present. Otherwise, when different nicotine products are compared in vitro, the order of the obtained release rates of nicotine may not reflect the order of the release rates of nicotine under normal user conditions.

Two experimental methods have been utilized to determine the nicotine delivery; an ex vivo method and an in vitro method. For both methods, a limited amount of aqueous liquid was to available release the nicotine from the pouch.

Ex Vivo.

Ex vivo is an experimental technique where the experiment is performed in vivo and the residual amount of the active component in the product is analyzed in vitro. In the current experiment, the pouch is kept under the upper lip for a certain time. It is thereafter taken out and the residual nicotine in the pouch is analyzed. This is performed for different use times (using a new pouch each time).

During use, different handling of the pouch by the user may result in different nicotine release rates. Therefore, the handling of the pouch during use should be standardized. Two different approaches have been applied. In the first approach the pouch is placed "in the front" under the upper lip and kept in that position during use. In the second approach the product is placed under the upper lip slightly on the left or on the right side. The product is then moved to the opposite side of the upper lip each fourth minute. In the second approach more saliva is available to the pouch.

After use the pouch is immediately placed in a tube containing 15.0 g purified water and it is shaken until all the residual nicotine in the pouch is dissolved into the water phase (minimum time 30 min).

In Vitro.

To a 140 mm Petri dish, a certain amount (4.0 g or 20.0 g) of purified water is added. A 110 mm filter paper (Munktell grade 00R) is placed in the middle of the dish. It is ensured that the filter paper is completely wetted by the purified water and that all air bubbles are removed. The pouch is placed flat in the middle of the filter paper for a certain time. The pouch absorbs some water which dissolves the nicotine salt and nicotine is released from the pouch into the external water phase. After use the pouch is immediately placed in a tube containing 15.0 g purified water and it is shaken until residual nicotine in the pouch is dissolved in the water phase (minimum time 30 min).

Analytical Method.

The residual content of nicotine in each individual nicotine pouch is determined in the same way for the ex vivo and the in vitro samples: The nicotine containing water phase in the test tube is diluted to a suitable concentration. The UV absorbance of the solution is determined at 260 nm. The nicotine concentration is calculated using a calibration curve and the residual amount of nicotine in the pouch is calculated. The UV method is non-specific for nicotine. Therefore, other substances in the pouch that also have absorption at 260 nm may introduce a minor error in the nicotine determination.

The nicotine content is also determined in the same way for a number of unused nicotine pouches from the same batch. From the following equation the fraction of released nicotine at the time t is calculated:

$$X_{released(t)} = (N_{unused} - N_{used(t)})/N_{unused}$$

$X_{released(t)}$ is the fraction of released nicotine for the used pouch at the time t $N_{unused}$ is the average amount of nicotine in unused pouches from the batch $N_{used(t)}$ is the residual amount of nicotine in the used pouch at the time t Results In Table 5 below $X_{released(6)}$ and $X_{released(16)}$ (the fraction of released nicotine for a used pouch after 6 minutes and 16 minutes use time) are presented. For example, when analyzed and calculated according to the methods described above, the Zonnic reference batch 09E56 has released 21 percent of the nicotine content after 16 minutes in the ex vivo test where the pouch is moved every fourth minute by the user.

needed for the products according to the disclosed invention compared to the reference products.

Figure 1:
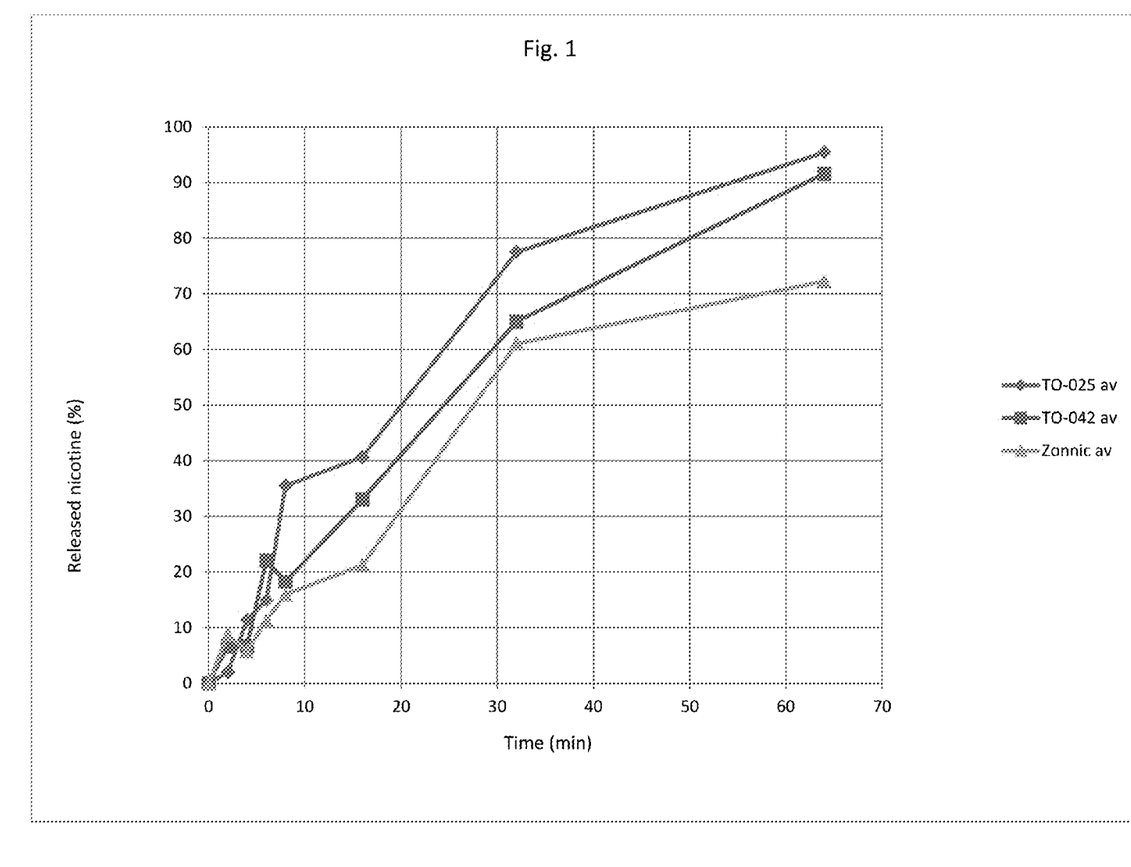
FIG. 1 shows the released nicotine after up to 64 minutes use time (in percent of the amount of nicotine in unused product). The test is an ex vivo study where the users change to position of the product under the upper lip with the tongue each fourth minute.

For some of the products the nicotine release was measured also at other use times, up to 64 minutes. It is anticipated that a normal use time for a pouch is about 30 to 60 minutes. It is desirable that the nicotine delivery is as complete as possible after a normal use time. In FIG. 1 the nicotine delivery for use times up to 64 minutes are presented for the batches described in Example 3 (named TO-025 in the Figure) and Example 4 (named TO-042 in the Figure), as well as Zonnic batch 09E56. The experimental conditions are an ex vivo study with two participants and the results are presented as average values of the two participants. It is the same two participants as in Table 5. The participants were instructed to change the position of the pouch every fourth minute from the left side to the right side of the upper lip. It is seen that the nicotine release for the samples according to the disclosed invention is, in general, higher than for the Zonnic samples. In particular, for the use times 32 minutes and 64 minutes the nicotine delivery is more complete for the formulations according to the disclosed invention than for Zonnic.

Figure 2:
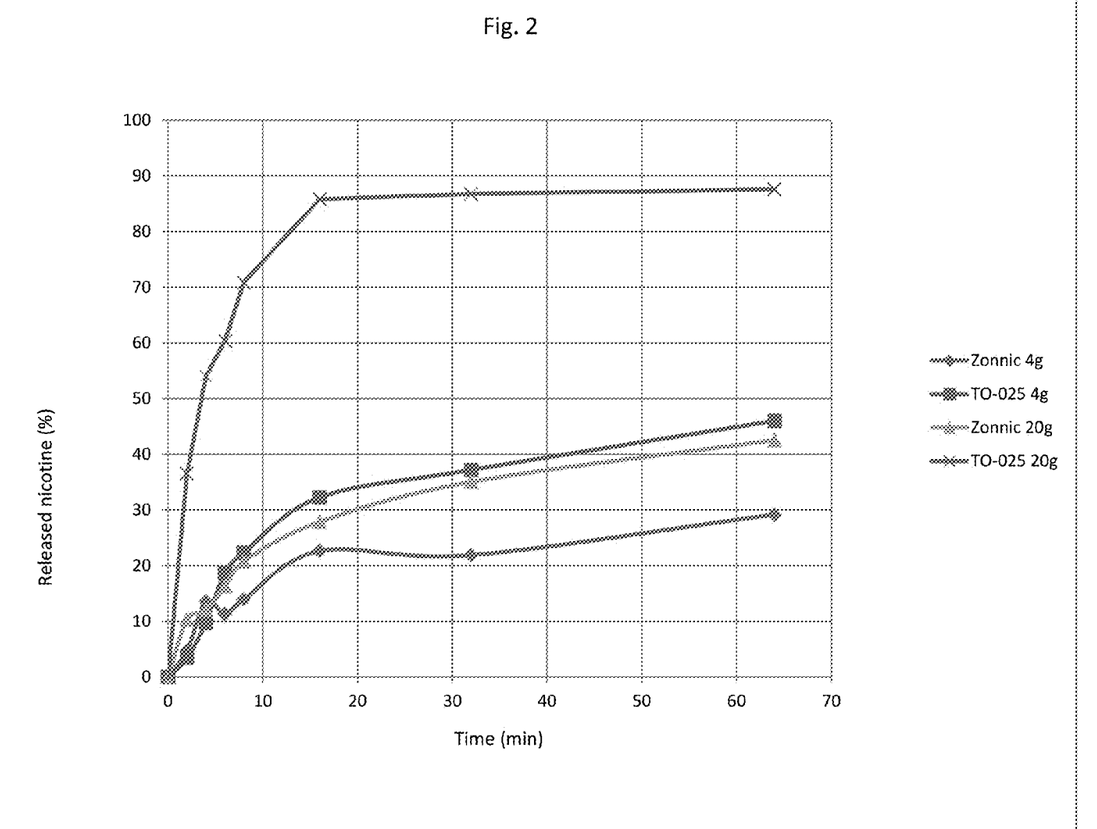
FIG. 2 shows the released nicotine after up to 64 minutes use time (in percent of the amount of nicotine in unused product). The test is an in vitro study where the product has been placed on a filter paper wetted with either 4.0 g or 20.0 g purified water.

In FIG. 2 the nicotine delivery for use times up to 64 minutes are presented for the batch described in Example 3 (named TO-025 in the Figure) and Zonnic batch 09E56. The experimental conditions are an in vitro study both with 4.0 g

TABLE 5

The released nicotine after 6 and 16 minutes use time for the experimental conditions described above (in percent of the average amount of nicotine in unused pouches for the batch)

| | | Ex vivo (**) | | | | In vitro | | | |
|---|---|---|---|---|---|---|---|---|---|
| | | Fixed position | | Moved every 4$^{th}$ minute | | 4.0 g water | | 20.0 g water | |
| Batch | Comments (*) | 6 min | 16 min | 6 min | 16 min | 6 min | 16 min | 6 min | 16 min |
| Zonnic 09E56 | Reference | — | — | 11 | 21 | 11 | 23 | 16 | 28 |
| Zonnic 10H23 | Reference | — | — | — | — | 14 | 24 | 21 | 34 |
| Zonnic 10H24 | Reference | — | — | — | — | 14 | 26 | 23 | 31 |
| 10R1 | Reference | — | — | — | — | — | — | 28 | 32 |
| 10R2 | Reference | — | — | — | — | — | — | 17 | 24 |
| 1F | Invention | — | — | — | — | — | — | 80 | 88 |
| 1I | Invention | — | — | — | — | — | — | 70 | 85 |
| 2 | Invention | — | — | — | — | — | — | 82 | 93 |
| 3 | Invention | — | — | 15 | 41 | 19 | 32 | 60 | 86 |
| 4 | Invention | 8 | 21 | 22 | 33 | 33 | 44 | 59 | 78 |
| 5 | Invention | — | — | — | — | — | — | 55 | 79 |
| 6 | Invention | — | — | — | — | — | — | 51 | 71 |
| 7 | Invention | — | — | — | — | — | — | 40 | 74 |
| 8 | Invention | — | — | — | — | — | — | 48 | 64 |

(*) "Reference" means reference samples. "Invention" means sample according to the disclosed invention
(**) Average values for two users (same users in all experiments)
(—) not measured For all experimental conditions, the nicotine release for the products according to the disclosed invention is more rapid than for reference products, both the reference product based upon the nicotine-cellulose combination and the reference product based upon the nicotine polacrilex complex.

Under the experimental conditions used in the in vitro test with 20.0 g purified water the most rapid nicotine release is obtained. After 16 minutes use time the nicotine release is rather complete for the products according to the disclosed invention, and in all cases, except one, it is above 70%. On the other hand for the reference products, the nicotine release is closer to 30-35% under the same experimental conditions. This shows that for an almost complete delivery of nicotine from the pouch a lower amount of liquid or a shorter time is water and 20.0 g water. The same pattern as in the ex vivo study emerge. The nicotine release is more rapid and more complete for the product according to the disclosed invention than for the Zonnic product.

Example 11

Products according to the disclosed invention have been stored at 25° C./60% RH for up to 3 months. Degradation products from nicotine were determined by reversed-phase liquid chromatography. The content of degradation products in a pouch was determined on a Gemini C18 column using a mobile phase consisting of phosphate buffer pH 10.0 and acetonitrile.

Matching of the retention time of degradation products in the samples and retention times for:
- blank solution (only mobile phase)
- samples with the same excipients, but without any nicotine bitartrate dihydrate
- samples of nicotine bitartrate dihydrate serves as an identity test for the degradation products.

The following samples were investigated:

TABLE 6

Compositions of the investigated samples (mg/pouch)

| | Components | 11A | 11B |
|---|---|---|---|
| P(*) | Nicotine bitartrate dihydrate | 9.22 | 9.22 |
| P | Maltitol | 80.9 | 78.9 |
| P | Avicel PH 200 | 95.0 | 95.0 |
| P | Sodium bicarbonate | 16.5 | — |
| P | Sodium carbonate | 9.5 | — |
| P | Encapsulated pH-adjuster(***) | — | 28.0 |
| P | Menthol Durarome | 10.0 | 10.0 |
| P | Acesulfame K | 0.85 | 0.85 |
| GL(**) | Wintergreen (Borgwaldt) | 7.0 | 7.0 |
| GL | Fresh Citrus Menthol (Borgwaldt) | 1.0 | 1.0 |
| GL | Kollidon 25 | 20.0 | 20.0 |

(*)Powder components
(**)Components of the granulation liquid
(***)16.5 mg sodium bicarbonate, 9.5 mg sodium carbonate och 2.0 mg Eudragit L 100

The two batches were manufactured in the following way:

The Encapsulated pH adjusting agent was manufactured according to the method described in Example 7.

The liquid components (GL) were mixed (together with ethanol corresponding to 30 mg/pouch) to a homogeneous solution. The powder components (P) were mixed in a planetary mixer and were sieved. The granulating liquid was slowly added to the powder mixture under stirring. The granulate was sieved and dried on a tray under ambient conditions.

The powder is filled into pouches (target fill weight 250 mg powder per pouch) using an in-house pouch filling machine. The pouch is made of long fiber paper. The filled pouches were stored in plastic containers permeable to moisture.

The following results were obtained:

TABLE 7

Observed degradation products after storage at 25° C./60% RH

| Storage conditions (months/temperature (° C.)/relative humidity | Sum of degradation products (%) | |
|---|---|---|
| | Batch 11A | Batch 11B |
| 1/25/60 | n.d.p.o. | n.d.p.o. |
| 2/25/60 | n.d.p.o. | n.d.p.o. |

(*) No degradation products observed

No degradation products from nicotine were observed in any of the samples stored at 25° C./60% RH after one or three months storage. All observed peaks in the chromatograms could be referred to nicotine bitartrate dihydrate, excipients or mobile phase.

This shows that the nicotine salt, nicotine bitartrat dihydrate, is stable also in the product according to the disclosed invention.

The invention claimed is:

1. A product for oral delivery of nicotine containing a core comprising a powder of
   a) at least one free nicotine salt wherein said nicotine salt is selected from the group consisting of nicotine hydrochloride, nicotine dihydrochloride, nicotine monotartrate, nicotine bitartrate, nicotine bitartrate dihydrate, nicotine sulphate, nicotine zinc chloride monohydrate and nicotine salicylate, and mixtures thereof
   b) at least one pH adjusting agent
   c) at least one filler
and a water insoluble pouch, wherein said pouch is permeable for saliva and therein dissolved parts of the powder, wherein said product upon contact with purified water gives a pH of at least 6.

2. The product according to claim 1, wherein said nicotine salt is water soluble.

3. The product according to claim 1, wherein said nicotine salt is nicotine bitartrate dihydrate.

4. The product according to claim 1, wherein said pH adjusting agent is selected from the group consisting of carbonates, monocarbonate, bicarbonate, sesquicarbonate, acetates, glycinates, gluconates, borates, glycerophosphates, citrates of alkaline metals, ammonium, phosphate systems, monohydrogenphosphate, dihydrogenphosphate, trihydrogenphosphate, metal hydroxides, sodium hydroxide, potassium hydroxide and mixtures thereof.

5. The product according to claim 1, wherein said pH adjusting agent is sodium bicarbonate, sodium carbonate and mixtures thereof.

6. The product according to claim 1, wherein said pH adjusting agent is encapsulated or embedded.

7. The product according to claim 1, wherein said pH adjusting agent is encapsulated or embedded with a polymer which physically separates the pH adjusting agent from the nicotine salt.

8. The product according to claim 1, wherein said filler is selected from the group consisting of polysaccharides, polyols, sugars, natural fibres, microcrystalline cellulose, cellulose and cellulose derivatives and mixtures thereof.

9. The product according to claim 1, wherein said product comprises at least one filler which is a sweetener or a flavoring agent.

10. The product according to claim 9 wherein said sweetener is selected from the group consisting of mono- di- tri- and polysaccharides, polyols, mannitol, maltitol, natural and synthetic sweeteners, sucrose, glucose, dextrose, maltose, fructose, saccharin, aspartame, acesulfame, sucralose, saccharin, cyclamates and mixtures thereof.

11. The product according to claim 1 wherein said flavoring agent is selected from the group consisting of bergamot, eucalyptus, orange, mandarin, citrus, lemon, peppermint, mint, menthol, liquorice, wintergreen, tobacco, coffee, vanilla, lime, apple, peach and mixtures thereof.

12. The product according to claim 1, wherein said pouch is manufactured from material selected from the group consisting of pharmaceutically acceptable membrane materials.

13. The product according to claim 1, wherein said product comprises nicotine in an amount of from 0.1 to 10 mg per unit dose calculated as nicotine base.

14. The product according to claim 10, wherein said product comprises nicotine in an amount of 0.5, 1.0, 1.5, 2.0, 2.5, 3.0, 3.5, 4.0, 4.5, 5.0, 6.0, 7.0, 8.0 or 9.0 mg per unit dose calculated as nicotine base.

15. The product according to claim 1, wherein said product comprises from 50 mg to 1000 mg of said powder.

16. The product according to claim 1, wherein said product comprises 100, 150, 200, 250, 300, 350, 400, 450, 500, 550, 600, 650, 700, 750, 800, 850, 900 or 950 mg of said powder.

17. A method of making a product comprising the steps of
a) providing a powder of at least on free nicotine salt and at least one pH adjusting agent and at least one filler, and a water insoluble pouch; and
b) obtaining a product according to claim 1.

18. The method according to claim 17 further comprising encapsulating or embedding the pH adjusting agent.

19. The method according to claim 17 further comprising granulating the powder.

* * * * *